(12) United States Patent
Golz-Berner et al.

(10) Patent No.: US 6,551,606 B1
(45) Date of Patent: Apr. 22, 2003

(54) COSMETIC PRODUCT CONTAINING ENZYMES

(75) Inventors: Karin Golz-Berner, Monaco (DE); Leonhard Zastrow, Monaco (DE)

(73) Assignee: Coty B.V. (NL)

( * ) Notice: Subject to any disclaimer, the term of this patent is extended or adjusted under 35 U.S.C. 154(b) by 0 days.

(21) Appl. No.: 10/018,213

(22) PCT Filed: Jun. 8, 2000

(86) PCT No.: PCT/DE00/01891
§ 371 (c)(1),
(2), (4) Date: Dec. 5, 2001

(87) PCT Pub. No.: WO00/76458
PCT Pub. Date: Dec. 21, 2000

(30) Foreign Application Priority Data

Jun. 10, 1999 (DE) .......................................... 199 27 229

(51) Int. Cl.⁷ .............................. A61K 6/00; A61K 7/06; A01N 65/00
(52) U.S. Cl. ........................ 424/401; 424/70.1; 424/74; 424/725
(58) Field of Search ............................... 424/401, 70.1, 424/74, 725

(56) References Cited

U.S. PATENT DOCUMENTS 5,229,130 A * 7/1993 Sharma et al. .............. 424/448
5,407,675 A * 4/1995 Etemad-Moghadam ..... 424/401
5,641,509 A * 6/1997 Gross et al. .................. 264/41
5,660,840 A * 8/1997 Pruett .......................... 424/401
5,891,440 A * 4/1999 Lansky ........................ 424/727
5,993,857 A * 11/1999 Menzel et al. ............... 424/450

OTHER PUBLICATIONS

Patent Abstracts of Japan, JP 05331045, Dec. 1993.*
Patent Abstracts of Japan, JP 56007712, Jan. 1981.*
Patent Abstracts of Japan, JP 62036304, Feb. 1987.*
A. Y. Leung, Encyclopedia of Common Natural Ingredients, 1996, pp. 299–300.*

* cited by examiner

*Primary Examiner*—Sreeni Padmanabhan
*Assistant Examiner*—Michael A. Willis
(74) *Attorney, Agent, or Firm*—Pendorf & Cutliff

(57) ABSTRACT

The invention relates to a cosmetic product that contains enzymes and has an intensive skin action, especially a regenerative effect The inventive cosmetic product contains 0.01 to 5 wt. % of a concentrate of the coconut milk of *Cocos nucifera*, containing peroxidase, lipase and protease; 0.1 to 10 wt. % of a plant milkwater, the plants being selected from the following group: banana, dandelion, convolvus, poppy, soya and mixtures thereof; and 0.01 to 5 wt. % of a glycerol extract of a mixture consisting of honey, rice hulls, rice hull oil and/or rice germ oil; with the remainder consisting of cosmetic auxiliary agents, active agents and carrier substances.

6 Claims, No Drawings

COSMETIC PRODUCT CONTAINING ENZYMES

This application is a 371 of PCT/DE00/01891, submitted Jun. 8, 2000.

FIELD OF THE INVENTION

The invention relates to a cosmetic product that contains enzymes and has an intensive skin action, especially a regenerative effect.

DESCRIPTION OF THE RELATED ART

There is already a number of known cosmetic products which are produced using animal milk or a derivate of lactic acid. DE-A-44 08 258, for example, discloses an oil/water emulsion containing whole milk, which emulsion contains polyethoxylated vitamin E as an emulsifier and has a viscosity of less than 100 Pa·s. DE-A-195 37 297 discloses cosmetic preparations containing growth factors which are produced from fresh or pasteurized milk and colostrum of cows and mares. Furthermore, EP-A-908171 discloses a dry, plant-based cleansing composition, in which various dried and crushed plants, which serve as detergent, foaming agent, foam enhancer, pigment and conditioner, are combined in a powder, *Cocos nucifera* being used as a foam enhancer.

SUMMARY OF THE INVENTION

The object of the invention is to provide a particularly mild cosmetic product which has soothing, regenerative and, at the same time, moisturizing properties.

According to the invention, a cosmetic product containing enzymes is provided, characterized in that it contains 0.01 to 5% by weight of a concentrate of the coconut milk of *Cocos nucifera*, containing peroxidase, lipase and protease; 0.01 to 10% by weight of a plant milkwater, the plants being selected from the group consisting of Musa (bananas), Taraxacum (dandelion), Convolvulus (Convolvulaceae), Papaver (poppy), soya and mixtures thereof; 0.01 to 5% by weight of a glycerol extract of a mixture consisting of honey, rice hulls, rice hull oil and/or rice germ oil; 99.97 to 80% by weight of cosmetic auxiliary agents, further active agents and carrier substances.

The plant milkwater according to the invention is obtained by pressing the fresh overground parts of the plants (stems, leaves, flowers), preferably of plants whose period of flowering is over, and it is used directly in the cosmetic product after removing solid components, if any. The term "plant milkwater" is used to refer to the usually milky latexes which are obtainable by cold pressing the relevant plant parts. Preferred plant milkwaters are those of dandelion and soya.

The enzymes contained in the coconut milk concentrate are highly effective with regard to several aspects. Lipase causes fatty acid triglycerides to break down into fatty acids and glycerol thus accelerating the liposysis of these substances and enabling them to be better discharged via the blood. If combined with protease, which plays a key role in the regeneration of the skin, the cells can be made to regenerate more rapidly, and due to the proteolytic effect, it is possible to promote and accelerate the regeneration of skin cells and the healing of wounds of the skin.

Peroxidase has scavenging properties and occurs in increased amounts in plants which are exposed to intense environmental stress such as ozone, air pollution, radiation, changed availability of nutrients. Peroxidase converts free OH radicals and peroxides into water and harmless substances thus achieving a noticeable anti-ageing effect with regard to skin cells.

The coconut milk concentrate, which may also be obtained by means of an extraction process using propylene glycol, may further contain cytokinin, which positively influences the regeneration of the skin as it stimulates cell division.

Altogether, the three active agents which are present in the cosmetic product containing enzymes according to the invention have an overall effect as regards the regeneration process of the skin, which is much stronger than the individual effects of the components. The said active agents are therefore particularly suitable for regeneration creams, anti-ageing creams and lotions, after-sun creams, fat reduction creams and firming creams.

In addition, the cosmetic product has excellent moisturizing, pH-adjusting and soothing effects, which, in combination with the above-mentioned properties, result in a very good feeling.

It is particularly worth mentioning that the cosmetic product according to the invention promotes the physiological hydration process of the skin. Measurements using a Corneometer® show a clear, long-lasting effect, i.e. in a measurement carried out after 8 hours, it was found that the increase in moisture achieved by applying a lotion had decreased by just 4–12%.

The cosmetic auxiliary agents and carrier substances, as they are commonly used in preparations similar to the cosmetic product at hand, include e.g. water, preservatives, vitamins, colourants, pigments having a colouring effect, scavengers, thickeners, softening substances, moisturizing substances, fragrances, alcohols, polyols, electrolytes, esters, gel-forming agents, polar and nonpolar oils, polymers, copolymers, emulsifiers, waxes, stabilizers.

Further additives and active agents contained in the cosmetic compositions may be vitamins or vitamin complexes, e.g. vitamin A or derivates thereof and/or vitamin E or derivates thereof; further biogenic plant extracts such as liposoluble gardenia extract, liposoluble carrot extract, paprika-LS extract, β-carotene, Lithospermum extract; organic sunscreens such as e.g. octyl methoxycinnamate; methyl gluceth-10 or methyl gluceth-20; and active deodorants such as triclosan or odour extinguishers such as Grillocin®.

The cosmetic active agents further include emulsifiers, inorganic and organic sunscreens, scavengers, enzymes, plant-based active agents, polymers, melanin, antioxidants, anti-inflammatory natural active agents, asymmetric lamellar aggregates loaded with oxygen according to WO94/00109; decomposition products of yeasts or plant substances produced by means of a gentle decomposition process using ultrasound according to WO94/13783, kaolin and kaolin modified with $SiO_2$ according to WO94/17588, a product obtained by gently decomposing a vegetable or animal starting material in an aqueous medium and subsequently condensing it with a sub-stoichiometric amount of a $C_{10}$–$C_{20}$ fatty acid halogenide according to WO96/29048.

Suitable esters or ethers are, for example (INCI names): dipentaerythrityl hexacaprilate/hexacaprate/tridecyl trimellitate/tridecyl stearate/neopentyl glycol dicaprylate dicaprate, propylene glycol dioctanoate-5, propylene glycol dicaprylate-2,30-dicaprate, tridecyl stearate/neopentyl glycol dicaprylate dicaprate/tridecyl trimellitate, neopentyl glycol dioctanoate, isopropyl myristate, diisopropyl dimer dilinoleate, trimethylpropane triisostearate, myristyl ether, stearyl ether, butyl ether, dicaprylyl ether, PPG1-PEG9 lauroyl glycol ether, PPG15 stearyl ether, PPG14 butyl ether, Fomblin HC25.

The cosmetic product containing enzymes may have the form of an O/W emulsion or a W/O emulsion. The oils used may be usual cosmetic oils such as a mineral oil; hydrogenated polyisobutene (INCI name: Hydrogenated Polyisobutene); squalane, both synthetic and made from natural products (INCI name: Squalane, e.g. Synthesqual®, Cosbiol®); cosmetic esters or ethers, which may be branched or linear, saturated or unsaturated; vegetable oils; or mixtures of two or more thereof.

Particularly suitable oils are, for example, mineral oils, hydrogenated polyisobutene, polyisoprene, squalane, tridecyl trimellitate, trimethylpropane triisostearate, isodecyl citrate, neopentyl glycol diheptanoate, PPG15 stearyl ether, calendula oil, jojoba oil, avocado oil, macadamia nut oil, castor oil, or a mixture of several thereof. Depending on which oils are selected, the cosmetic properties of the solid composition, such as the degree of transparency, softness, hardness, spreading effect, are influenced.

The cosmetic product may also have the form of a gel. Suitable gel-forming agents include carbomer, xanthan gum, carrageenan, gum arabic, guar gum, agar-agar, alginates and tylosen, carboxymethyl cellulose, hydroxyethyl cellulose, certain polyacrylates, polyvinyl alcohol, polyvinyl pyrrolidone, montmorrillonite, etc.

As a rule, a number of compounds may be used as an emollient in the cosmetic product according to the invention, such as stearyl alcohol, glyceryl monoricinoleate, glyceryl monostearate, propane-1,2-diol, butane-1,3-diol, cetyl alcohol, isopropyl isostearate, stearic acid, isobutyl palmitate, oleyl alcohol, isopropyl laurate, decyl oleate, octadecane-2-ol, isocetyl alcohol, cetyl palmitate, silicone oils such as dimethylpolysiloxane, isopropyl myristate, isopropyl palmitate, polyethylene glycol, lanolin, cocoa butter, vegetable oils such as maize oil, cotton seed oil, olive oil, mineral oils, butyl myristate, palmitic acid, etc.

Antioxidants which may be used in the invention include vitamins such as vitamin C and derivates thereof, for example ascorbyl acetates, ascorbyl phosphates and ascorbyl palmitates; vitamin A and derivates thereof; folic acid and derivates thereof; vitamin E and derivates thereof such as tocopheryl acetate; flavones or flavonoids; amino acids such as histidine, glycine, tyrosine, tryptophan and derivates thereof; carotenoids and carotenes such as e.g. α-carotene, β-carotene; uric acid and derivates thereof; α-hydroxy acids such as citric acid, lactic acid, malic acid; stilbenes and derivates thereof, etc.

DETAILED DESCRIPTION OF THE INVENTION

In a preferred embodiment of the invention, the cosmetic product containing enzymes contains 0.01 to 2% by weight of lactic acid. In this way, other active agents can be made to penetrate much better into the skin.

It may be preferable for the preparations according to the invention that the cosmetic product contained in them be encapsulated in asymmetric lamellar aggregates, these aggregates consisting of phospholipids and fluorocarbon or fluorocarbon mixtures loaded with oxygen and their fluorocarbon content being in the range of 0.2 to 100% by weight/volume, wherein the said phospholipid has a phosphatidylcholine content of more than 30 and up to 99% by weight, and wherein the ability to penetrate into the skin of these aggregates is a function of the critical solubility temperature of the fluorocarbons.

The content of these aggregates may be in the range of 0.05 to 20% by weight, relative to the total weight of the cosmetic product.

In addition, the cosmetic preparation may also contain aggregates of the type described above, but which are loaded with oxygen only.

These aggregates are oxygen carriers thus enabling oxygen to penetrate into the skin and, as a result, a better oxygen supply of the skin. These aggregates are produced by high-pressure homogenizing phosholipids, such as lecithin from soya and eggs or synthetic phospholipids or partly hydrated phospholipids whose phosphatidylcholine content is higher than 30 and up to 99% by weight, with perfluorinated or highly fluorinated carbon compounds or mixtures thereof which are able to transport gases such as oxygen and carbon dioxide. Besides phosphatidylcholine, lysolecithines in a concentration of 0.1 to 10% by weight and/or charged phospholipids, such as phosphatidylethanolamine, n-acetylphosphatidylethanolamine or phosphatidic acid, in a concentration of 0.1 to 30% by weight may be present during this process.

In contrast to the known aqueous liposomes (vesicles), these phospholipid-stabilized aggregates carry hydrophobic fluorocarbons in their core, which are able to transport oxygen. Their interfacial chemical stabilization is achieved primarily by means of an inversely arranged monolayer and, if necessary, a subsequent building-up of bilayers. Due to their special structure, these new aggregates are termed asymmetric lamellar oxygen carriers. Their exceptional collochemical stability is probably attributable to their lamellar structure and the surface charge of the aggregates. The latter depends on the selection of suitable phospholipids, both natural and synthetic ones, and mixtures thereof. An advantageous effect as described above is caused primarily by phosholipids, particularly phosphatidylcholine in the said concentration of 30 to 99% by weight, in combination with lysolecithines in a concentration of 0.1 to 10% by weight and/or charged phospholipids in a concentration of 0.1 to 30% by weight. The said effect of the phospholipids is verified by corresponding negative zeta potentials and by means of measuring the charge densities (while titrating with a cationic polyelectrolyte). The main criterion as regards the use of the fluorocarbon aggregates is their ability to penetrate into the skin, which is a function of the critical solubility temperature of the selected fluorocarbons or fluorocarbon mixtures (for the use of asymmetric lamellar aggregates see also DE-C-42 21 255).

Another active agent which may be contained in the cosmetic product according to the invention are finely divided, magnetically hard single-domain particles (monocrystals) having a high coercivity and particle sizes in the range of 100 to 1,200 nm, with or without the above-mentioned asymmetric lamellar aggregates, and which magnetically hard particles are, in particular, barium hexaferrite and/or strontium hexaferrite produced according to the glass crystallization method, i.e. the growing of single crystals from a quenched glass melt (see WO95/03061 and WO98/44895).

It is advantageous, that a further active agent contained in the cosmetic product be kaolin according to WO96/17588, which has been modified with spherical $TiO_2$ particles or $SiO_2$ particles whose particle size is <5 µm, the spherical particles making up 0.5 to 10% by weight of the kaolin mixture. In this way, the preparation feels very soft on the skin and has an additional anti-inflammatory effect.

The content of modified kaolin may be in the range of 0.1 to 6% by weight, relative to the total amount of the cosmetic product.

The cosmetic product may also contain pigments, pigment mixtures or powders having a pigment-like effect, including such ones which have a gloss effect, which may comprise, for example, iron oxides, titanium (di)oxide, mica, kaolin, talc, mica-titanium oxide, mica-titanium oxide-iron oxide, bismuth oxychloride, nylon globules, ceramic globules, expanded and non-expanded synthetic polymer powders, powdery natural organic compounds such as ground solid algae, encapsulated and non-encapsulated cereal starch and mica-titanium oxide-organic colourant.

Further, it is advantageous to add water- and/or oil-soluble UVA or UVB filters, or both, to the compositions according to the invention. Advantageous oil-soluble UVB filters include derivates of 4-aminobenzoic acid such as 4-(dimethylamino)-benzoic acid-(2-ethylhexyl)ester; esters of cinnamic acid such as 4-methoxy cinnamic acid-(2-ethylhexyl)ester; derivates of benzophenone such as 2-hydroxy-4-methoxybenzophenone; derivates of 3-benzylidene camphor such as 3-benzylidene camphor.

Preferred oil-soluble UV filters are benzophenone-3, butyl methoxybenzoylmethane, octyl methoxycinnamate, octyl salicylate, 4-methylbenzylidene camphor, homosalate and octyl dimethyl PABA.

Water-soluble UVB filters are, for example, sulfonic acid derivates of benzophenone or of 3-benzylidene camphor, or salts such as the Na- oder K-salt of 2-phenylbenzimidazol-5-sulfonic acid.

UVA filters include derivates of dibenzoylmethane such as 1-phenyl-4-(4'-isopropylphenyl)propane-1,3-dion.

Preferred sun filters are inorganic pigments on the basis of metal oxides such as $TiO_2$, $SiO_2$, ZnO, $Fe_2O_3$, $ZrO_2$, MnO, $Al_2O_3$, which may also be used in the form of mixtures.

The cosmetic product may also contain shellac in its aqueous phase, the content of pure shellac being in the range of 0.1 to 20% by weight in an O/W emulsion, in the range of 0.1 to 15% by weight in a W/O emulsion, and in the range of 0.1 to 10% by weight in a hydrogel. This water-soluble shellac is produced according to WO99/06011 or WO99/06488.

Another additive for the cosmetic product according to the invention is a combination of active agents comprising a) a product enzymatically extracted from the maritime plankton *Artemia salina*, the extraction product consisting of phosphorylated nucleotides whose main component is diguanosine tetraphosphate; b) D-myo-inosit-1,4,5-triphosphate; c) glycan; the ratio of a to b to c being in the range 1 to 0.1–50 to 0.1–30. This combination has a synergy effect against aggressive environmental influences as it naturally strengthens the immune system of the skin, stimulates the regeneration of the skin, and provides protection against UV radiation by improving the keratin barrier.

Another additive for the cosmetic product according to the invention is a preparation of active agents which has a high radical protection factor and contains a product obtained from the bark of *Quebracho blanco* by means of an extraction process and subsequent enzymatic hydrolysis, which product contains at least 90% by weight of proanthocyanidin oligomers and no more than 10% by weight of gallic acid and is contained in micro-capsules, and a silkworm extract obtained by means of an extraction process and which contains the peptide cecropine, amino acids and a vitamin mixture, and a non-ionic, cationic or anionic hydrogel or hydrogel mixture, and one or more phospholipid(s) and water.

The concentrate of the coconut milk of *Cocos nucifera*, which is used for the invention, is a commercial product offered by Greentech S.A., St. Beauzire Cedex, France, under the name of Cocozyme®. The coconut milk concentrate is a pale yellow liquid which is soluble in water and alcohol.

1 kg of the above-mentioned glycerol extract is produced from 5 g of honey, 50 g of rice hulls, 10 g of rice germ oil or rice hull oil (Extrapone Honey/Rice Blend GW® by Dragoco, Holzminden, Germany, and Extrapone Honey Rice Milk®).

The cosmetic preparation according to the invention may be used e.g. in suncreams, sun gels, after-sun products, day creams, night creams, masks, body lotions, cleansing milk, make-up, body powder, eye cosmetics, hair masks, hair conditioners, hair shampoos, shower gels, shower oils, bath oils. The said products are manufactured in a way known to those having the ordinary skill in the art.

The invention will hereinafter be explained more precisely by means of examples. All quantities are given in per cent by weight, unless indicated otherwise.

EXAMPLE 1

Moisturizing Cream for all Skin Types

| | |
|---|---|
| Phase A | |
| Steareth- 2 | 2.5 |
| Steareth-21 | 1.5 |
| Beeswax | 6.0 |
| Jojoba oil | 1.5 |
| Phase B | |
| Water | q.s. ad 100 |
| Copolymer | 0.5 |
| Glycerol | 3.0 |
| Phase C | |
| Triethanolamine | 0.5 |
| Phase D | |
| Preservative | 0.5 |
| Phase E | |
| Coconut milk concentrate | 0.5 |
| Coconut (*Cocos nucifera*) water | |
| Plant milkwater of | 1.0 |
| soya plants (Glycine spp.) | |
| Glycerol extract from honey, | 0.5 |
| rice hulls and rice hull oil | |
| Water & glycerol & rice (*Oryza sativa*) bran | |
| extract & PEG-40 hydrogenated castor oil | |
| & trideceth-9 & rice (*Oryza sativa*) bran oil | |
| & honey extract | |
| Phase F | |
| Perfume | 0.2 |

In order to produce this cream, phases A and B are heated separately up to a temperature of 60 to 70° C., phase A is then stirred into phase B, and both phases are thoroughly homogenized with each other. Then, phase C is added and homogenized for a short while. The mixture is cooled down to a temperature of approx. 40° C., and phases D to F (in this order) are added one after the other while stirring.

EXAMPLE 2

2-in-1 Shampoo and Gel

| | |
|---|---|
| Water | q.s. ad 100 |
| Sodium laureth sulfate | 53.0 |
| Disodium EDTA | 0.1 |
| Polyquaternium-7 | 1.0 |
| Panthenol | 0.1 |
| Preservative | 0.3 |
| Coconut milk concentrate | 5.0 |
| Plant milkwater of dandelion (Taraxacum spp.) | 10.0 |
| Glycerol extract from honey, rice hulls and rice germ oil | 3.0 |

The above substances are mixed at room temperature adding one after the other and stirring until a homogeneous mixture is obtained.

EXAMPLE 3

Moisturizing Cream Having a Long-lasting Effect

| | |
|---|---|
| Phase A | |
| Steareth-2 | 2.0 |
| Steareth-21 | 2.21 |
| Stearic acid | 1.8 |
| Stearyl alcohol | 3.2 |
| Phase B | |
| Water | q.s. ad 100 |
| Glycerol | 5.0 |
| Kaolin modified with $SiO_2$ * | 5.0 |
| Phase C | |
| Asymmetric lamellar aggregates ** | 10.0 |
| Plant milkwater of dandelion (Taraxacum spp.) | 2.0 |
| Plant milkwater of soya plants (Glycine spp.) | 1.5 |
| Glycerol extract from honey, rice hulls and rice germ oil | 1.0 |
| Coconut milk concentrate | 1.0 |
| RPF complex *** | 1.5 |
| Phase D | |
| Preservative | 1.0 |
| Phase E | |
| Perfume | q.s. |

* kaolin according to WO96/17588;  aggregates according to WO94/00109; * complex of active agents according to WO99/66881 and which has a high radical protection factor Phases A and B are heated separately up to a temperature of approx. 65° C. and mixed with each other while stirring. The mixture is cooled down to approx. 40° C. while stirring, and then phases C, D and E are stirred in.

EXAMPLE 4

Face and Body Gel with SFP 15

| | |
|---|---|
| Phase A | |
| Water | q.s. ad 100 |
| Crosspolymer | 0.1 |
| Glycerol | 2.0 |

-continued

| | |
|---|---|
| Phase B | |
| Triethanolamine | 0.1 |
| Phase C | |
| Octyl methoxycinnamate | 7.5 |
| Octyl salicylate | 5.0 |
| Butyl methoxydibenzoylmenthane | 3.0 |
| Phase D | |
| Stabileze QM PVM/MA decadiene crosspolymer | 1.5 |
| Phase E | |
| Shellac * | 5 |
| Kaolin modified with $SiO_2$ ** | 1.5 |
| RPF complex *** | |
| Sun Marine complex + | 1.0 |
| Glycerol extract from honey, rice hulls and rice germ oil | 0.5 |
| Coconut milk concentrate | 0.5 |
| Plant milkwater of dandelion (Taraxacum spp.) | 0.5 |
| Lactic acid | 0.4 |
| Perfume | q.s. |
| Preservative | 1.0 |

* shellac according to WO996011, Example 2;  kaolin according to WO96/17588; * complex of active agents according to WO99/66881 and which has a high radical protection factor; + yeast decomposition product according to WO98/25584, Example 1

The phases were mixed at room temperature adding one after the other in the above order and thoroughly homogenized.

What is claimed is:

1. A cosmetic product containing enzymes, wherein it contains 0.01 to 5% by weight of a concentrate of the coconut milk of *Cocos nucifera*, containing peroxidase, lipase and protease; 0.01 to 10% by weight of a plant milkwater, the plants being selected from the group consisting of Musa, Taraxacum, Convolvulus, Papaver, Glycine and mixtures thereof; 0.01 to 5% by weight of a glycerol extract of a mixture consisting of honey, rice hulls, rice hull oil and/or rice germ oil; 99.97 to 78% by weight of cosmetic auxiliary agents, active agents and carrier substances.

2. A cosmetic product containing enzymes according to claim 1, wherein it contains 0.01 to 2% by weight of lactic acid.

3. A cosmetic product containing enzymes according to claim 1, wherein the plant milkwater is obtained by cold pressing the overground parts of the plants.

4. A cosmetic product containing enzymes according to claim 1, wherein the plant milkwater is a milkwater of dandelion or soya, or a mixture thereof.

5. A process for enhancing the regenerative properties of a skin regeneration cosmetic preparation, said method comprising adding to said preparation ingredients such that said preparation comprises 0.01 to 5% by weight of a concentrate of the coconut milk of *Cocos nucifera*, containing peroxidase, lipase and protease; 0.01 to 10% by weight of a plant milkwater, the plants being selected from the group consisting of Musa, Taraxacum, Convolvulus, Papaver, Glycine and mixtures thereof; 0.01 to 5% by weight of a glycerol extract of a mixture consisting of honey, rice hulls, rice hull oil and/or rice germ oil; and 99.97 to 78% by weight of cosmetic auxiliary agents, active agents and carrier substances.

6. A cosmetic product containing enzymes, said product containing:

0.01 to 5% by weight of a concentrate of the coconut milk of *Cocos nucifera*, said concentrate containing peroxidase, lipase and protease;

0.01 to 10% by weight of a plant milkwater from a plant selected from the group consisting of Musa, Taraxacum, Convolvulus, Papaver, and Glycine, and mixtures thereof;

0.01 to 5% by weight of a glycerol extract of a mixture consisting of two or more of honey, rice hulls, rice hull oil and rice germ oil; and 99.97 to 78% by weight of cosmetic auxiliary agents, active agents and carrier substances.

* * * * *